United States Patent [19]
Friese et al.

[11] Patent Number: 5,670,032
[45] Date of Patent: Sep. 23, 1997

[54] ELECTRO-CHEMICAL MEASURING SENSOR WITH A POTENTIAL-FREE SENSOR ELEMENT AND METHOD FOR PRODUCING IT

[75] Inventors: Karl-Hermann Friese, Leonberg; Helmut Weyl, Schwieberdingen; Siegfried Nees, Neckarwestheim; Hans-Martin Wiedenmann, Stuttgart, all of Germany

[73] Assignee: Robert Bosch GmbH, Stuttgart, Germany

[21] Appl. No.: 592,381
[22] PCT Filed: Jul. 9, 1994
[86] PCT No.: PCT/DE94/00791
§ 371 Date: Jan. 25, 1996
§ 102(e) Date: Jan. 25, 1996
[87] PCT Pub. No.: WO95/04273
PCT Pub. Date: Feb. 9, 1995

[30] Foreign Application Priority Data

Jul. 27, 1993 [DE] Germany .................. 43 25 157.9
Dec. 15, 1993 [DE] Germany .................. 43 42 731.6

[51] Int. Cl.$^6$ ................................................ G01N 27/26
[52] U.S. Cl. ........................................................ 204/424
[58] Field of Search ................................... 204/424–429

[56] References Cited

U.S. PATENT DOCUMENTS

| | | | |
|---|---|---|---|
| 4,383,906 | 5/1983 | Sano et al. | 204/428 |
| 4,569,748 | 2/1986 | Yamekawa et al. | 204/428 |

*Primary Examiner*—Bruce F. Bell
*Attorney, Agent, or Firm*—Spencer & Frank

[57] ABSTRACT

An electro-chemical measuring sensor (10) for determining the oxygen content of gases, in particular for determining the oxygen content in exhaust gases of internal combustion engines, with a potential-free disposed sensor element (14). The sensor element (14) has an oxygen-ion-conducting solid electrolyte body (23), preferably in the shape of a pipe or tube closed at one end, which has an exterior electrode (25) disposed on the exterior surface with a strip conductor (27) on the side toward the contact and also extending on the exterior surface, and which is inserted by means of a sealing ring (20) in a metal housing (11). The sensor element (14) has an electrically insulating layer (21) at least in the area of the sealing ring (20), which covers at least the strip conductor (27) in the direction toward the housing (11). The insulating layer (21) is formed from a mixture of a crystalline, non-metallic material and a glass-forming material. In the course of production the insulating layer (21) is subjected to a thermal treatment above the melting temperature of the glass-forming material, in the course of which the insulating layer (21) forms a glaze filled with the crystalline, non-metallic material.

23 Claims, 2 Drawing Sheets

ELECTRO-CHEMICAL MEASURING SENSOR WITH A POTENTIAL-FREE SENSOR ELEMENT AND METHOD FOR PRODUCING IT

BACKGROUND OF THE INVENTION

This application is a 371 of PCT/DE94/00791 filed Jul. 9, 1994.

The invention is based on an electro-chemical measuring sensor for determining the oxygen content of gases, in particular for determining the oxygen content of exhaust gases of internal combustion engines, including a potential-free arranged sensor element having an oxygen-ions-conducting solid electrolyte body, preferably in the form of a pipe closed at one end, and electrodes with electrically conducting connectors, with the sensor element being inserted with a sealing ring into a metal housing and with at least one electrically conducting connector facing the housing being electrically insulated with respect to the housing by an electrically insulating layer in the area of the sealing ring. Electro-chemical measuring sensors are embodied, for example, in the so-called finger construction, wherein a solid electrolyte body is sealingly fixed as a closed pipe in a metal housing. Among the finger sensors, a differentiation is made between potential-free and potential-bound measuring sensors. With potential-bound measuring sensors, the trace of the exterior electrode is brought into contact with the housing by means of an electrically conducting sealing ring. With potential-free measuring sensors, each electrode connection is directly supplied to a control device, so that no electric contact with the housing is permitted. In both cases a seal between the solid electrolyte body and the housing must be realized.

A potential-free measuring sensor is known from DE-OS 25 04 206, wherein a plurality of electrically insulating, ceramic seal rings made of sintered corundum with >90% $Al_2O_3$ are employed, and which provide a hermetically sealed, electrically insulating connection between the solid electrolyte body and the metal housing. Such a seal is structurally very elaborate and also relatively prone to risks because of the multiple parallel seal with three sealing rings.

It is furthermore already known from DE-OS 26 19 746 to cover the trace on the solid electrolyte body with glazing, in particular in the areas of lower temperature.

SUMMARY AND ADVANTAGES OF THE INVENTION

In contrast to the known electro-chemical measuring sensors for determining the oxygen content of gases, the measuring sensor in accordance with the invention includes a potential-free arranged sensor element having an oxygen-ions-conducting solid electrolyte body, preferably in the form of a pipe closed at one end, and electrodes with electrically conducting connectors, with the sensor element being inserted with a sealing ring into a metal housing, with at least one electrically conducting connector facing the housing being electrically insulated with respect to the housing by an electrically insulating layer in the area of the sealing ring, and with the insulating layer being formed of a mixture of a crystalline, non-metallic material and a glass-forming material such that a glaze filled with the crystalline, non-metallic material is formed by heating. This sensor according to the invention has the advantage that sealing elements which are electrically conducting can be used for sealing the sensor element in the housing, for example a metal sealing ring or a graphite sealing ring or graphite package. By employing these compact seals, exhaust gas, water and/or fuel are prevented from reaching the interior of the sensor element. The insulating layer has a great mechanical sturdiness in respect to pressure peaks which are created by the sealing ring in the course of the joining process. The method of the invention has the advantage that it can be integrated into the manufacturing process of sensor elements. The application processes of the insulating layer are possible by means of proven technology, for example, rolling on, spraying a suspension, flame spraying, plasma spraying, printing or the like.

Advantageous further developments and improvements of the measuring sensor in accordance with the invention, and of the method of the invention are possible by means of the steps recited in the dependent claims. A particularly good electrical insulation is achieved if the electrically insulating layer is made from an oxide-ceramic material and an earth alkali silicate. A glaze filled with ceramic is produced from the mixture by means of a thermal after-treatment.

To prevent the introduction of the glass-forming material into the material of the electrical connection, it is practical to dispose an intermediate layer, which preferably consists of the material of the solid electrolyte body, under the insulating layer, at least in the area of the electrically conducting connector. The material of the insulating layer offers a great insulation resistance at high application temperatures in comparison with the layers of the solid electrolyte material. The raw materials used are cheaply available.

To prevent or reduce pressure peaks of a sealing element, for example, a metal sealing ring, on the insulating layer, it is furthermore particularly advantageous to provide the insulating layer with a cover layer at least in the area of the sealing ring. The formation of fissures in the insulating layer is prevented thereby, which otherwise negatively affect the insulating effect and sturdiness of the insulating layer. The cover layer used furthermore acts as a diffusion barrier for interfering cations, for example heavy metal cations such as $Cu^+$, $Cu^{2+}$, $Fe^{2+}$ which emanate from the sealing element (for example a Cu-coated steel sealing ring) and can cause a defined electrical conductivity in the insulating layer and in this way can destroy the insulating effect at least at high temperatures.

The course of the process can be integrated into the manufacturing process particularly efficiently by co-sintering the insulating layer or the further applied layers with the solid electrolyte body. The insulating layer has in addition excellent adhesion which comes about in particular by co-sintering. A greatly matched thermal expansion of the insulating layer to the material of the solid electrolyte body has a positive effect on the layer adhesion in addition. Furthermore, the dense insulating layer protects the solid electrolyte body against hydro-thermal attacks, in particular in the low temperature range (150° to 300° C.). The structural stability of the solid electrolyte body is improved by this.

BRIEF DESCRIPTION OF THE DRAWINGS

Exemplary embodiments of the invention are represented in the drawings wherein.

DETAILED DESCRIPTION OF THE EXEMPLARY EMBODIMENTS

Figure 1:
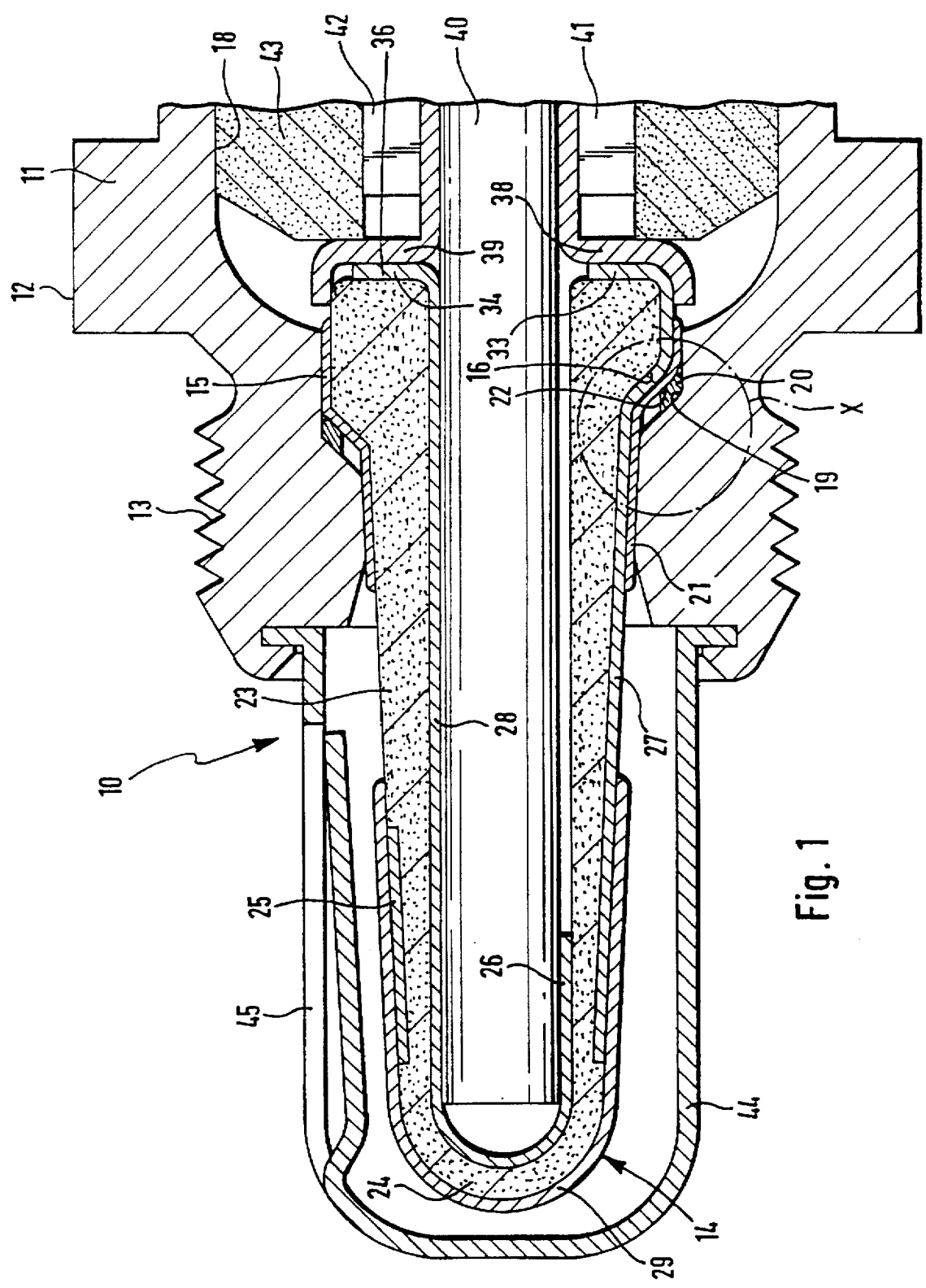
FIG. 1 shows a longitudinal section through the portion of the measuring sensor on the exhaust gas side.

The electro-chemical measuring sensor 10 represented in FIG. 1 has a metal housing 11 which has a key hexagon 12 and a thread 13 on its outside as fastening means for the installation of a pipe for the gas to be measured, not shown. The housing 11 has a longitudinal bore 18 with a seal seat 19 supporting a sealing ring 20. A sensor element 14 with a shoulder 16 embodied on a bulge-shaped head 15 rests on the seal seat 19 provided with the sealing ring 20. A sealing face 22 is formed on the bulge-shaped head 15 of the sensor element on the side toward the sensor element between the sealing ring 20 and the sensor element 14. The seal seat 19 itself forms a sealing face on the side toward the housing. The sealing zone X being formed on the sealing ring 20 is shown in an enlargement in FIGS. 2 to 4.

In the instant example, the sensor element 14 is an oxygen sensor, known per se, which is preferably used for measuring the partial oxygen pressure in exhaust gases. The sensor element 14 has a tube or pipe-shaped solid electrolyte body 23, whose end section toward the gas to be measured is closed off by means of a bottom 24. A layer-like, gas-permeable measuring electrode 25 is disposed on the outside of the solid electrolyte body 23 which is exposed to the gas to be measured, and a gas-permeable and layer-like reference electrode 26 is disposed on the side facing the interior and is exposed to the reference gas, for example air. The measuring electrode 25 is connected with a first electrode contact 33 by means of a measuring electrode strip conductor 27 and the reference electrode 26 is connected with a second electrode contact 34 by means of a reference electrode strip conductor 28. The electrode contacts are respectively located on a front face 36 formed by the open end of the solid electrolyte body 23. A porous protective layer 29 has been placed over the measuring electrode 25 and partially over the measuring electrode strip conductor 27. The strip conductors 27, 28 are advantageously constructed as cermet layers and co-sintered.

The sensor element 14 projecting out of the longitudinal bore 18 of the housing 11 on the side of the gas to be measured is surrounded by a spaced-apart protective pipe 44, which has openings 45 for the gas to be measured to enter and leave and which is fastened on the end of the housing toward the gas to be measured. The interior of the sensor element 14 is filled by a rod-shaped heating element 40, for example, which is fastened in a manner not shown remote from the gas to be measured and is provided with line connections.

A first contact element 38 rests on the first electrode contact 33 and a second contact element 39 rests on the second electrode contact 34. The contact elements 38, 39 are shaped in such a way that they rest against the pipe-shaped heating element and are connected with a measuring electrode connector 41 and a reference electrode connector 42. The connectors 41, 42 are connected with connecting cables, not shown, and are conducted to the outside to a measuring or control device.

An insulating sleeve 43 is furthermore inserted into the longitudinal bore 18 of the housing 11 and in a preferred manner consists of a ceramic material. The insulating sleeve 43 is pressed on the contact elements 38, 39 by a mechanical means, not shown, by means of which the electrical connection with the electrode contacts 33 and 34 is created.

To provide an electrically insulating and gas-tight fastening of the sensor element 14 in the housing 11, the shoulder 16 formed on the bulge-shaped head 15 is seated by means of the sealing ring 20 on the housing 11. Metal or graphite are particularly suited as the material for the sealing ring 20 for sealing the interior of the sensor element 14. Because of their great density, these materials are particularly impermeable to gas, water and motor fuel. A steel sealing ring with, for example, a copper coating of 10 micrometers or a nickel coating of 20 micrometers is practical.

Figure 2:
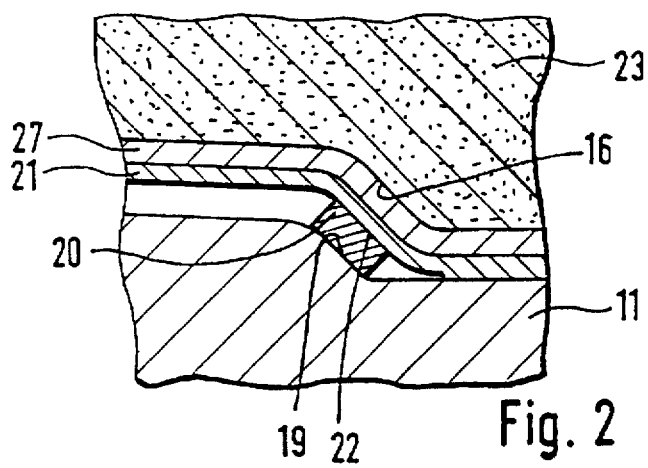
FIGS. 2, 3 and 4 show exemplary embodiments of an enlarged sealing zone X in accordance with FIG. 1.
Figure 3:
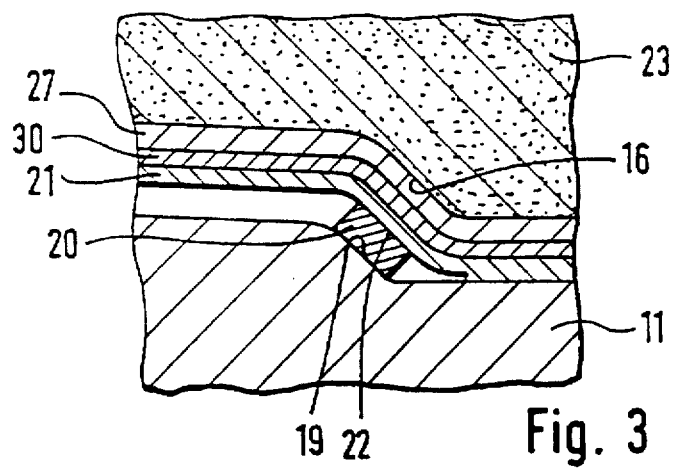
Figure 4:
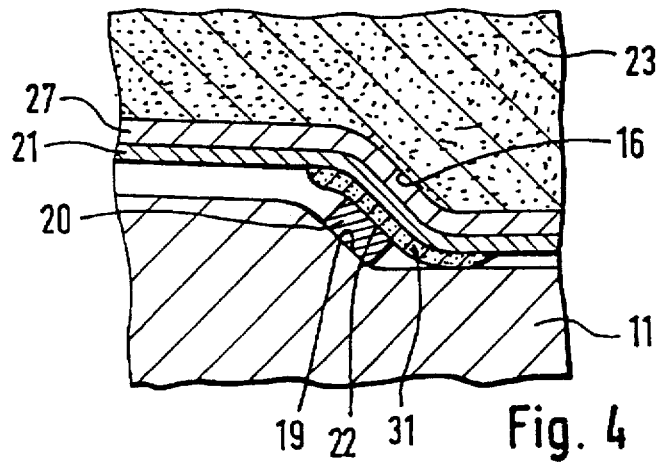

A clearer representation of the sealing zone X between the sensor element 23 and the housing 11 ensues from the respective FIGS. 2 to 4. However, a prerequisite for the employment of an electrically conducting sealing ring 20 is that the sensor element 14 is potential-free in respect to the metal housing 11. For this purpose the strip conductor 27 in a first exemplary embodiment in FIG. 2 is covered with an electrically insulating layer 21, particularly in the area of the sealing face 22 on the side toward the sensor. The insulating layer 21 has a layer thickness of 20 to 100 micrometers. In the instant exemplary embodiment the insulating layer 21 is drawn over the entire area of the strip conductor 27 and around the circumference of the solid electrolyte body 23 which adjoins the housing 11. However, it is also conceivable to limit the insulating layer 21 only to the area of the sealing face 22, or to extend the insulating layer 21 on the side of the gas to be measured as far as the protective layer 29, which is advantageous because it is possible by means of this to prevent shunts, caused by deposits of soot and/or other conducting materials from the exhaust gas, if the protective layer is sufficiently electrically insulated, for example plasma-sprayed Mg-spinel.

A further exemplary embodiment in accordance with FIG. 3 consists in covering the strip conductors 27 with an intermediate layer 30, preferably of the material of the solid electrolyte body, and to place the insulating layer 21 in accordance with the already described exemplary embodiment over the intermediate layer 30, wherein the intermediate layer is suitably also co-sintered. Here the intermediate layer 30 has the function that the glass-forming material of the insulating layer 21 is not diffused into the material of the strip conductor 27 and in this way affects the conductivity of the strip conductor 27.

The material of the insulating layer 21 is selected in such a way that it withstands the pressure forces of the sealing ring 20 which occur when joining the sensor element 14 to the housing 11, and that furthermore it will tolerate temperatures of at least up to 700° C. in the area of the joint. This is achieved in that a crystalline, non-metallic material which is homogeneously distributed forms a bearing support frame in a glaze layer and the transformation temperature of the glass phase lies above the application temperature.

The specific electrical resistance of the crystalline, non-metallic material advantageously has at least ten times the value of the specific electrical resistance of the solid electrolyte body. Usable materials are: $Al_2O_3$, Mg-spinel, forsterite, stabilized $ZrO_2$, CaO- and/or $Y_2O_3$-stabilized $ZrO_2$ with small stabilizer contents, advantageously with maximally ⅔ of the stabilizer oxide of the full stabilization, non-stabilized $ZrO_2$ or $HfO_2$ or a mixture of these materials.

An earth alkali silicate, for example Ba-Al silicate, is used as the glass-forming material. The Ba-Al silicate has a thermal expansion coefficient of, for example, $\geq 8.5 \times 10^{-6}$ $K^{-1}$. The barium can be replaced by strontium up to 30 atom %.

The earth alkali silicate can be introduced as a pre-melted glass frit or as a glass-phase raw material mixture, wherein the latter is advantageously relieved to the greatest part of water of crystallization, carbonate or similar annealing losses in a calcination process. A small portion (<10 weight-%) of a glass-forming mixture of raw materials is advantageously added to the glass frit. The material mixture may contain electrically conducting impurities only up to maximally 1 weight-%. This relates in particular to $Na_2O$, $K_2O$, $Fe_2O_3$, $TiO_2$, $Cu_2O$ or similar semi-conducting oxides. The content of electrically conducting impurities lies advantageously below 0.2 weight-%.

A third exemplary embodiment ensues from FIG. 4, wherein a cover layer 31 is disposed over the electrically insulating layer 21 in the area of the sealing layer 22 on the side toward the sensor element, so that the sealing ring 20 rests against the cover layer 31 on the side toward the sensor element. The layers following on the side toward the sensor element correspond to the exemplary embodiment in FIG. 1. However, it is also conceivable to embody the layers on the side toward the sensor element in accordance with the exemplary embodiment in FIG. 3. The cover layer 31 is a thick ceramic layer, which preferably consists of the material of the solid electrolyte body 23, for example of yttrium-stabilized $ZrO_2$. To create a thick layer, the flux portion of the ceramic base material is selected to be less than 10 percent, wherein no flux addition at all creates the thickest layer. The cover layer 31 need not have an insulating resistance, instead it can have a noticeable electron and/or ion conductivity. In the case of electrical conductivity the cover layer 31 must not overlap the insulating layer 21. The layer thickness of the cover layer 31 is advantageously between 10 and 50 micrometers. It has been shown to be furthermore advantageous to adapt the thermal expansion coefficient of the cover layer 31 to approximately $\pm 2 \times 10^{-6} K^{-1}$ to the thermal expansion coefficient of the solid electrolyte body.

Various examples for the composition and production of the insulating layer 21 and the cover layer 31 will be described below:

Example 1

Composition of the inorganic raw material mixture:

60 weight-% of alumina (99.5 weight-% of $Al_2O_3$, 0.1 weight-% of $Na_2O$), specific surface 15 $m^2/g$ 40 weight-% of Ba—Al silicate glass powder (53 weight-% of BaO, 5 weight-% of $Al_2O_3$, 42 weight-% of $SiO_2$, specific surface 5 $m^2/g$).

The raw materials are homogenized and ground open over two hours in a ball mill with 90% $Al_2O_3$ grinding balls. Afterwards an aqueous slip is prepared with 500 g of a raw material mixture of alumina and Ba—Al silicate glass, 500 ml of distilled water and 25 ml of an aqueous polyvinyl alcohol solution. The slip is ground in a ball mill with 90% $Al_2O_3$ grinding balls over a grinding period of 1.5 hours.

The slicker is applied by brushing to the solid electrolyte body 23, which was pre-sintered at 1000° C., of partially stabilized $ZrO_2$ (5 mol-% of $Y_2O_3$) in the area of the insulating layer 21 in accordance with FIG. 1. Following this, the slip is co-sintered together with the solid electrolyte body 23 for approximately 3 hours at 1450° to 1500° C., so that the insulating layer in accordance with FIG. 1 is formed. For mounting the measuring sensor, the sensor element 14 is placed on the sealing ring 20. In this embodiment the insulation resistance at a sealing ring temperature of 500° C. lies above 300 kOhm. By comparison, the insulating resistance of a sensor element 14 which was only provided with a coating of $ZrO_2$ partially stabilized with 5 mol-% of $Y_2O_3$ in the area of the sealing zone 22, lies below 5 kOhm at a sealing ring temperature of 500° C.

Example 2

This example differs in respect to the raw material mixture in Example 1 in that in place of 40 weight-% of Ba—Al silicate glass powder the following composition was selected:

38 weight-% of Ba—Al silicate glass powder, 1 weight-% of kaolin, 1 weight-% of barium carbonate ($BaCO_3$, chemically pure), Insulation resistance>300 kOhm.

Example 3

This composition of the raw material mixture differs in respect to Example 1 in that in place of the Ba—Al silicate glass powder the following components were employed:

40 weight-% of a calcinate of:

11 weight-% of kaolin, 34 weight-% of quartz (99% of $SiO_2$) and 55 weight-% of $BaCO_3$ (chemically pure)

The components are ground up for two hours in a ball mill with 90% $Al_2O_3$ grinding balls and are calcined as bulk material in corundum capsules in an oxidizing atmosphere at 1000° C. for two hours and subsequently ground open again as mentioned.

Insulation resistance>300 kOhm.

Example 4

The composition of the raw material mixture differs from that of Example 1 and Example 3 as follows:

70 weight-% of alumina and 30 weight-% of calcinate,

Insulation resistance>300 kOhm.

Example 5

As in Example 4, however, in place of alumina with:

70 weight-% of partially stabilized $ZrO_2$ with 3.5 weight-% of MgO (35% monoclinal), Specific surface 7 $m^2/g$ Insulation resistance>20 kOhm.

Example 6

As in Example 3, but with:

50 weight-% of alumina, 50 weight-% of calcinate,

Insulation resistance>300 kOhm.

Example 7

As in Example 3, but with:

85 weight-% of alumina, 15 weight-% of calcinate,

Insulation resistance>200 kOhm.

Example 8

The composition of the raw material mixture corresponds to Example 6. However, in this case the slip is sprayed by means of a glazing pistol on the solid electrolyte body finished by dense sintering at 1450° to 1500° C. The insulating layer is subsequently sintered in over two hours at 1300° to 1350° C. in an oxidizing atmosphere.

Insulation resistance>100 kOhm.

Example 9

The composition corresponds to Example 7, wherein the alumina here contains the following components:

99.3% of $Al_2O_3$, 0.3% of $Na_2O$,

Specific surface 2.5 $m^2/g$,

Insulation resistance>100 kOhm.

Example 10

The composition corresponds to Example 6, however, the following components in place of alumina:

50 weight-% of monoclinal zircon oxide powder without addition of a stabilizer (99.5% of $ZrO_2$+$HfO_2$)

Specific surface 8.5 m²/g

Insulation resistance>100 kOhm.

Example 11

The composition corresponds to Example 6, however, with the following components in place of alumina:

60 weight-% of Mg-spinel powder ($MgOAl_2O_3$) with <0.5 weight-% of free MgO and <0.1 weight-% of $Na_2O$.

Specific surface 8 m²/g.

Insulation resistance>300 kOhm.

Example 12

The application of the insulating layer 21 of the solid electrolyte body 23 takes place as described in Example 1. The insulating layer 21 is dried at, for example 120° C., in a forced-air oven for approximately one hour. After this the cover layer 31 of partially stabilized zircon oxide with 5 mol-% of $Y_2O_3$ is applied. Spray suspensions or pressure pastes, known per se from the prior art, are used for producing the cover layer 31, wherein the cover layer 31 is brushed on in the instant example. Finally, the solid electrode body 23 with the electrodes and the electrode strip conductors, the insulating layer 21 and the cover layer 31 is co-sintered for three hours at 1450° to 1500° C.

Example 13

The production of the insulating layer 21 takes place as in Example 12, but pre-sintering of the solid electrolyte body 23 and the insulating layer 21 is performed at approximately 1000° C. in place of the drying process. Subsequently the cover layer 31 is applied and co-sintering in accordance with Example 12 is performed.

Example 14

The production takes place in accordance with Example 13, however, in this case the insulating layer 21 consists of 50 weight-% of alumina and 50 weight-% of Ba—Al silicate powder.

Example 15

The insulating layer 21 consists of the material in accordance with Example 1. After applying the insulating layer 21, co-sintering is performed. This is followed by the application by means of a flame spraying method of the cover layer 31 made of fosterire powder. Subsequently tempering is performed over two hours at 1300° C.

Example 16

The production of the insulating layer 21 takes place in accordance with Example 15. In this case the cover layer 31 consists of magnesium spinel and is applied by means of a flame spraying method without subsequent tempering. In this case the layer thickness of the cover layer 31 is suitably selected to be 10 micrometers.

Example 17

In this case the composition of the raw material mixture corresponds to Example 6. The slip is sprayed on in accordance with Example 8 by means of a glazing pistol on the solid electrolyte body finished by sintering at 1450° to 1500° C. The insulating layer 21 is thereafter sintered in over two hours at 1300° C. This is followed by producing the cover layer 31 in accordance with Example 16.

We claim:

1. An electro-chemical measuring sensor for determining the oxygen content of gases, including a potential-free arranged sensor element having an oxygen-ions-conducting solid electrolyte body and electrodes with electrically conducting connectors, wherein the sensor element is inserted with a sealing ring into a metal housing and at least one electrically conducting connector facing the housing is electrically insulated in respect to the housing by an electrically insulating layer in the area of the sealing ring, wherein the insulating layer is formed of a mixture of a crystalline, non-metallic material and a glass-forming material such that a glaze filled with crystalline, non-metallic material is formed by heating, and wherein the glass-forming material is an earth alkali silicate glass.

2. A measuring sensor in accordance with claim 1, wherein one of the two materials respectively constitutes at least 10 vol.-% of the mixture.

3. A measuring sensor in accordance with claim 1, wherein the crystalline, non-metallic material is selected from the group consisting of $Al_2O_3$, Mg-spinel, forsterite, MgO-stabilized $ZrO_2$, CsO- and/or $Y_2O_3$-stabilized $ZrO_2$, non-stabilized $ZrO_2$, $HfO_2$ and mixtures thereof.

4. A measuring sensor in accordance with claim 1, wherein the insulating layer has a thermal expansion coefficient which is at least approximately matched to the thermal expansion coefficient of the material of the solid electrolyte body.

5. A measuring sensor in accordance with claim 4, wherein the crystalline, non-conducting material has a thermal expansion coefficient of greater than $6 \times 10^{-6}$ $K^{-1}$.

6. A measuring sensor in accordance with claim 1, wherein the glass-forming material is a barium-aluminum silicate glass.

7. A measuring sensor in accordance with claim 6, wherein up to 30 atom-% of barium are substituted by strontium.

8. A measuring sensor in accordance with claim 1, wherein the electrically insulating layer is placed around the solid electrolyte body at least in the area of the sealing ring.

9. A measuring sensor in accordance with claim 1, wherein the insulating layer extends up to a protective layer covering the measuring electrode.

10. A measuring sensor in accordance with claim 1, wherein the layer thickness of the insulating layer is 10 to 100 micrometers.

11. A method for producing a potential-free disposed sensor element for a measuring sensor in accordance with claim 1, wherein the mixture of the insulating layer, consisting of the crystalline, non-conducting material and the glass-forming material, is subjected to a thermal treatment above the melting temperature of the glass-forming material.

12. A method in accordance with claim 11, wherein the glass-forming material is introduced into the mixture in the form of a pre-melted glass frit.

13. A method in accordance with claim 12, wherein the glass frit is used with an addition of a glass-forming raw material mixture less than 10%.

14. A method in accordance with claim 11, wherein the glass-forming material is introduced into the mixture in the form of a mixture of glass-forming raw materials.

15. A method in accordance with claim 11, wherein the glass-forming raw materials are relieved of water of crystallization, carbonate and similar heating losses in a calcination process in a proportion of greater than 90%.

16. A method in accordance with claim 11, wherein the thermal treatment of the insulating layer is performed by co-sintering with the solid electrolyte body.

17. A measuring sensor in accordance with claim 1 wherein the solid electrolyte body is in the form of a pipe closed at one end.

18. An electro-chemical measuring sensor for determining the oxygen content of gases including a potential-free arranged sensor element having an oxygen-ions-conducting solid electrolyte body and electrodes with electrically conducting connectors, wherein the sensor element is inserted with a sealing ring into a metal housing and at least one electrically conducting connector facing the housing is electrically insulated with respect to the housing by an electrically insulating layer in the area of the sealing ring, wherein the insulating layer is formed of a mixture of a crystalline, non-metallic material and a glass-forming material such that a glaze filled with the crystalline, non-metallic material is formed by heating, and wherein an intermediate layer is disposed between the electrically conducting connector and the insulating layer at least in the area of the electrically insulating section.

19. A measuring sensor in accordance with claim 18, wherein the intermediate layer consists of the material of the solid electrolyte body.

20. An electro-chemical measuring sensor for determining the oxygen content of gases including a potential-free arranged sensor element having an oxygen-ions-conducting solid electrolyte body and electrodes with electrically conducting connectors, wherein the sensor element is inserted with a sealing ring into a metal housing, wherein at least one electrically conducting connector facing the housing is electrically insulated with respect to the housing by an electrically insulating layer in the area of the sealing ring, wherein the insulating layer is formed of a mixture of a crystalline, non-metallic material and a glass-forming material such that a glaze with the crystalline, non-metallic material is formed by heating, and wherein a ceramic cover layer is placed over the insulating layer, at least in the area of the sealing ring, to absorb mechanical pressure forces of the sealing ring.

21. A measuring sensor in accordance with claim 20, wherein the cover layer is a dense ceramic layer, to whose material a flux agent of less than 10% has been added prior to sintering.

22. A measuring sensor in accordance with claim 21, wherein the material of the cover layer consists of the material of the solid electrolyte body.

23. A measuring sensor in accordance with claim 20, wherein the thickness of the cover layer is 10 to 50 micrometers.

* * * * *